United States Patent
Peng

(10) Patent No.: US 7,339,671 B2
(45) Date of Patent: Mar. 4, 2008

(54) APPARATUS AND METHOD FOR MONITORING BIOLOGICAL CELL CULTURE

(76) Inventor: Hong Peng, 42874 Via Navarra, Fremont, CA (US) 94539

(*) Notice: Subject to any disclaimer, the term of this patent is extended or adjusted under 35 U.S.C. 154(b) by 212 days.

(21) Appl. No.: 11/160,058

(22) Filed: Jun. 7, 2005

(65) Prior Publication Data

US 2005/0254055 A1 Nov. 17, 2005

Related U.S. Application Data

(63) Continuation-in-part of application No. 10/761,943, filed on Jan. 20, 2004, now abandoned.

(51) Int. Cl.
*G01N 21/00* (2006.01)
*G01N 21/01* (2006.01)

(52) U.S. Cl. ................. 356/338; 356/244
(58) Field of Classification Search ........ 356/337–343, 356/432–444; 435/34–39, 288.1, 286.7, 435/290.2
See application file for complete search history.

(56) References Cited

U.S. PATENT DOCUMENTS

| | | | |
|---|---|---|---|
| 4,250,394 A | 2/1981 | O'Connor | |
| 4,725,148 A | 2/1988 | Endo et al. | |
| 4,893,935 A | 1/1990 | Mandel et al. | |
| 5,182,193 A | 1/1993 | Mishima et al. | |
| 5,432,061 A * | 7/1995 | Berndt et al. | 435/34 |
| 5,518,923 A * | 5/1996 | Berndt et al. | 435/287.3 |
| 5,858,769 A | 1/1999 | Di Guiseppi et al. | |
| 5,888,805 A | 3/1999 | Endo et al. | |
| 6,929,953 B1 * | 8/2005 | Wardlaw | 436/63 |
| 2003/0146162 A1 * | 8/2003 | Metzel et al. | 210/668 |

* cited by examiner

*Primary Examiner*—Tarifur Chowdhury
*Assistant Examiner*—Tara S Pajoohi

(57) ABSTRACT

An apparatus and method for real-time and on-line monitoring the cell growth and concentration in a dynamic cell culture environment, with techniques that suppressing noise from ambient light, non-uniform scattering distribution, bubble and interface reflection effects in the dynamic environment.

20 Claims, 7 Drawing Sheets

APPARATUS AND METHOD FOR MONITORING BIOLOGICAL CELL CULTURE

This patent application is a CIP application for U.S. patent application Ser. No. 10/761,943, filed on Jan. 20, 2004 now abandoned. This patent application is entitled to the benefit of a provisional Patent Application: 60/581,088, filed on Jun. 18, 2004.

BACKGROUND OF THE INVENTION

Biological culture is an important bioprocess for cell growth. The growth curve of cells can demonstrate the effect of environmental chemicals, pH, temperature, and other parameters and endogenous factors on the corresponding cells. Here the biological cells include microorganism cells (bacteria, yeast, or fungi), human cells, animal cells and insect cells. Real-time and on-line monitoring a biological cell culture, especially in a dynamic environment such as an incubator/shaker, is quite valuable in a variety of fields including biotechnology, pharmaceutics, clinical medicine, agriculture and food industry.

Existing biological cell culture equipments range from simple incubators, incubated shakers, or shakers to sophisticated and expensive bioreactors. Among them, the incubator/shakers for small to medium volume (<5000 ml) biological culture containers like culture flasks are the most widely used equipments in laboratories. Here the incubator/shakers is a term for incubated shakers or shakers. These incubated/shakers have shaking platforms which can move horizontally with an orbital circle. This conventional cell culture method has been used for many many years. However, so far, there is no a real-time and on-line culture monitoring system being developed for detecting the growth curve or concentration of biological cell culture with such small to medium volume culture equipments.

The concentration of biological cells is one of direct indicators for the biological culture status, apart from pH, dissolved oxygen and dissolved carbon dioxide. The two most common techniques of measuring the concentration of the cells are spectrophotometery and hemocytometry. The spectrophotometer technique is to detect the turbidity of biological culture media in term of optical density (OD) and the hemocytometer technique is to count the biological substance number in a diluted biological medium.

The principle of spectrophotometer is that the intensity of the light which is transmitted through a biological medium containing an absorbing and scattering substance like cells and proteins is decreased by that fraction which is absorbed and scattered, and this fraction can be detected and measured photo-electrically.

Generally, there are two kinds of concentration measurement using the spectrophotometery method for biological cell culture. First one is to utilize a special cuvette or a test tube with a small volume (about 1 ml). To perform such conventional measurement for a growing biological substance like microorganisms in a flask, it usually requires withdrawing a small sample from the biological medium and putting the sample in a cuvette or a test tube for a spectrophotometer measurement. This kind of measurement is discrete and can cause a disruption for biologic culture. The second is to utilize a stick-shape probe with a light emitter and a light sensor or optical fibers. This kind of spectrophotometer is usually designed for bioreactors. Although this kind of device can perform continuous measurement, it is still very difficult for this kind of spectrophotometers to operate in a shaking environment. The measurement requires submerging the probe in a biological medium and sterilization is always required.

These existing measurements become very tedious and even impossible when a real-time and on-line continuous concentration measurement is required especially when biological cells are in growing and shaking environment. A real-time, on-line and automatic measurement of biological cell growth curve, concentration or even other properties such as pH and $CO_2$ in an incubator/shaker culture environment will allow culture process to be very efficient and productive and can solve logistic problems and save time and efforts for users.

SUMMERY OF THE INVENTION

The object of this invention is to provide a culture monitoring system including an apparatus and method for real-time and on-line monitoring biological cell culture in an incubator/shaker environment other than in a bioreactor. One of cell culture properties for monitoring is the cell concentration of biological culture medium.

Another object of this invention is to innovate existing incubator/shakers by integrating the incubator/shakers with the culture monitoring system that can perform real-time and on-line monitoring of one or more biological culture media simultaneously. Furthermore, based on the concentration measurements with the monitoring system, the biological culture growth rate can be altered purposely by automatically controlling and regulating culture environment parameters such as the temperature, shaking speed of the incubator/shaker or both.

The above objects can be achieved by utilizing a light scattering technique that detecting the turbidity or other measurable properties of the biological culture medium in a transparent container. With a proper arrangement of a light source and a photodetector outside of the container and some digital data processing techniques, signal fluctuation problems caused mainly by ambient light, non-uniform scattering distribution, bubble and air-medium interface reflection can be minimized.

BRIEF DESCRIPTION OF THE DRAWINGS

FIG. 1a shows a top view or a down vertical view of the probe without drawing a flask. FIGS. 1b & 1c show the cross section of the probe from the point of view A and view B with a flask. View A is a horizontal view. View B is not a horizontal view or a vertical view. It has an angle relative to the vertical view.

DESCRIPTION OF THE INVENTION

Figure 1A:
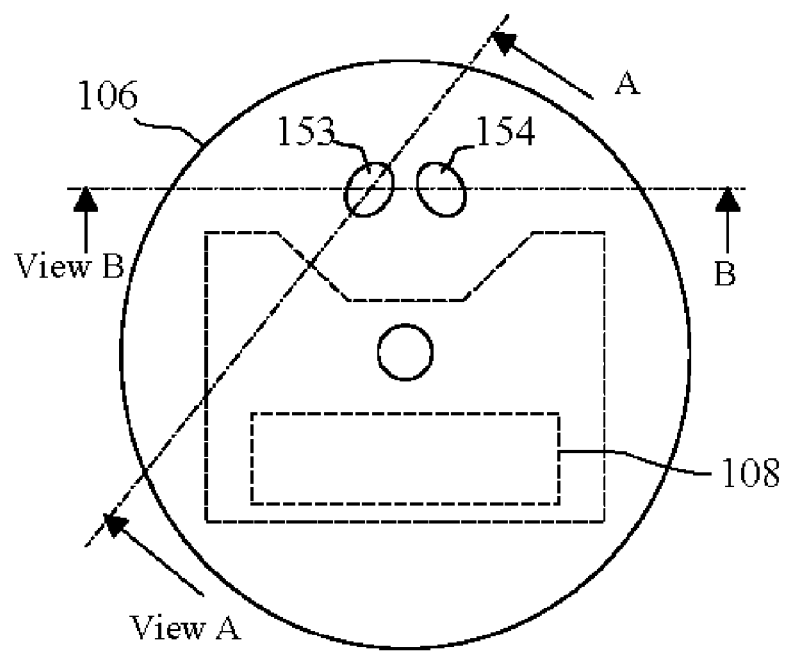
FIG. 1a-c. Schematic diagrams of a light scattering probe for shaking flask culture.

This invention presents an apparatus and method that providing a wide range, real-time and on-line continuous detection for some properties of a biological culture medium without submerging a probe in the medium or withdrawing a small medium sample from the container. The properties of the biological culture medium for monitoring in this invention are the turbidity, cell concentration, growth curve, growth rate, fluorescence, protein inclusion bodies and viable cell concentration. The primary mesaurable property of the biological culture medium is the turbidity. The container can be a regular flask, a beaker, a bottle or a specially designed container. The container can be made from transparent glass, crystal or plastics.

One of key parts of this invention is to utilize a light scattering technique that is not limited to transmission detection. The most common method of measuring the turbidity of a biological culture medium is to utilize a transmission optical density technique. The transmission technique requires a short and constant light path in a culture medium to achieve a linear and repeatable measurement requirements. This requirement makes it hard to be utilized for ordinary culture containers unless specially designed culture containers, such as an Erlenmeyer flask with a small stick-out volume, are used. However a light scattering with a small or large angle relative to incident light beam could be utilized for the turbidity detection with ordinary culture containers such as culture flasks.

When light transmits through a biological medium containing a biological substance such as microorganism, cells, DNA or protein, the light can be mostly scattered other than absorbed. The scattered light intensity also depends on the concentration of biological media. It should be noted that the scattering and absorption properties of the biological media could also depend on other factors such as light wavelength, biological substance size, color, and refractive index. The spatial distribution of the scattered light intensity also depends on the properties of biological media.

For a simple case that light scattering is ruled by Rayleigh theory, assuming light scatters uniformly to any angle direction and the light is mostly scattered other than absorbed, the scattered light intensity from a point on its light path should be proportional to the density of a biological medium and input light intensity at that point. If the input light intensity at that point is constant, the scattered light intensity is proportional to the density at that point. So it is easy to understand that the entry place for the light entering a biological medium is an area to have such simple density-proportion property for the scattering light if the light source intensity is constant. However in other area in the light path, the incident light intensity at that area varies with the density of biological cells.

Another key part of this invention is to apply the light scattering detection technique to a biological culture medium even in a shaking environment. The part of invention includes the techniques of fixing the position of a scattering detection probe relative to a biological culture container during a detection period and further reducing signal fluctuation noise caused mainly by ambient light, non-uniform scattering distribution, bubble and air-medium interface reflection.

The signal fluctuation noise is a challenging problem in shaking environment. For a detector with the light scattering technique, there are many noise sources such as electronic noise, thermal drift noise, ambient light noise and shaking medium noise. However the most critical noise is the shaking medium noise. The shaking medium noise comes from the bubbles in biological medium, light reflection and refraction from shaking air-medium interface and scattering fluctuation of turbulent biological medium. This shaking medium noise depends on the arrangement of incident light beam and the culture medium container. In this invention, one of key points is to fix the position of the probe with respect to the container and arrange the incident light beam submerging in the medium and not going through the air-medium interface to reduce the shaking medium noise.

Figure 1B:
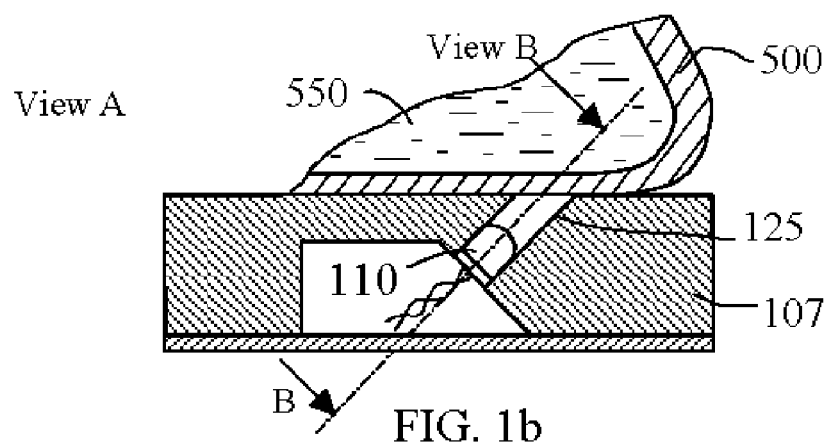
Figure 1C:
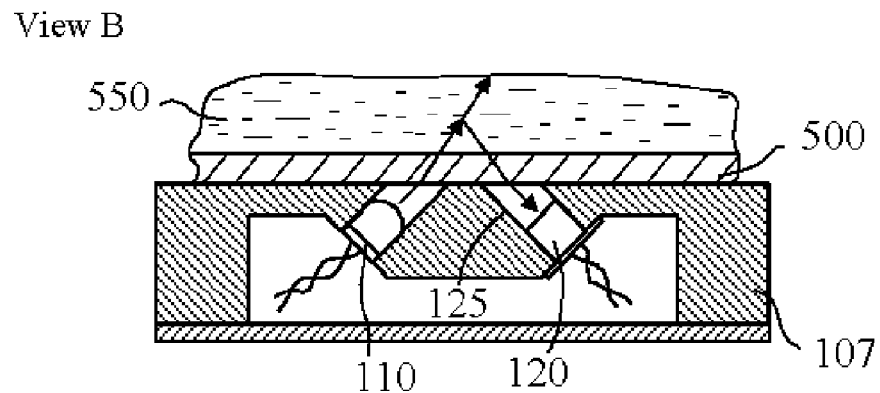

In the first embodiment, a light scattering probe 106 is schematically shown in FIG. 1a-c. The probe includes a probe enclosure 107, electronic circuitry 108, at least a light source 110 and at least a photodetector 120. Electronic circuitry 108 usually includes a power supply or driver for light source 110, photodetector sensing circuitry with a pre-amplifier for photodetector 120, or/and temperature control circuitry for light source 110 or/and photodetector 120. Source 110 can be a monochromic source like a semiconductor laser source, Light Emission Diode (LED) or a non-monochromic source like ordinary flash lamp, tungsten lamp and broadband LED. The source 110 can be in UV, visible or NIR wavelength. The photodetector 120 can be a photodiode, a phototransistor, a photoconductive cell (CdS), a photomultiplier tube or a CCD detector. The detector 120 is to detect the scattered light from a medium 550 through a transparent wall of a biological medium container 500. The scattered light could be in different wavelength from that of light source 110 such as fluorescence. With help of a fluorescent indicator for pH or $CO_2$, photodetector 120 with an optical filter may be able to detect pH or $CO_2$ in medium 550. The medium container 500 can be a typical culture flask, beaker, bottle or specially designed container with a small, medium or large volume. In this invention, only culture flasks such as Erlenmeyer flasks are presented. It is important that source 110 and detector 120 are arranged to near the bottom corner of container 500 as shown in FIG. 1b. The incident light beam from source 110 has a small angle relative to the horizontal plane so that the light beam can be always submerged in biological medium without going through the interface between the medium and air in container 500 when the container 500 with the biological medium and attached probe 106 are in an orbital shaking circumstance. By using a light guide tunnel 125, lens or both, the photodetector 120 is aimed or focused to detect the scattering light from an area that is close to the entry position of the light beam in the medium.

In the first embodiment as shown in FIG. 1a-c, the probe 106 is constructed to detect a wide-angle scattering. The angle can be around the right angle or a larger angle relative to the incident light beam. The incident light beam is designed to interact with culture medium 550 around the bottom corner of the container 500. A top view of probe 106 is shown in FIG. 1a and two apertures 153 and 154 are located near the edge of probe 106. The aperture 153 is for outgoing light beam of source 110 and the aperture 154 is for the photodetector 120. FIGS. 1b and 1c schematically show the cross sections of the probe 106 from the point of view A and B, respectively.

In the first embodiment, to reduce the influence of incident light reflection from the container wall at the entry area as well as ambient light influence, a narrow incident light beam and a narrow detection angle are required. For light sources 110, a narrow light beam can be formed using a light guide tunnel 125, lens or both. The photodetector 120 can be constructed with narrow detection angular characteristics so that it can only detect scattering light from medium at the light path of source 110. In addition, a simple light tunnel 125 or/and lens can help photodetector 120 aim to the detection area and narrow the viewing angle. The distance between the two apertures and light tunnel length should be carefully designed to avoid the direct reflection of incident light from the container wall to the photodetector 120.

Figure 2A:
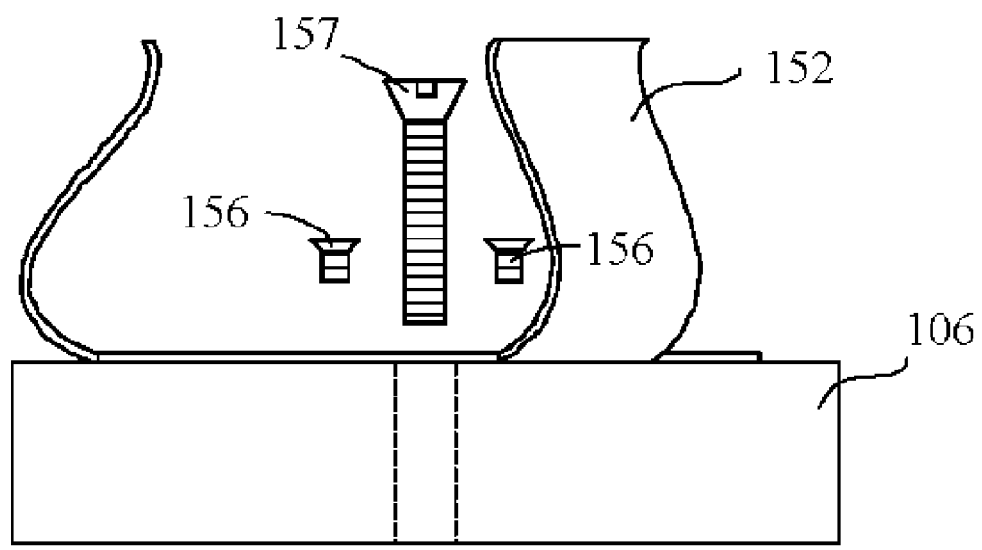
FIGS. 2a & 2b Schematic diagrams of a light scattering probe with a flask clamp.
Figure 2B:
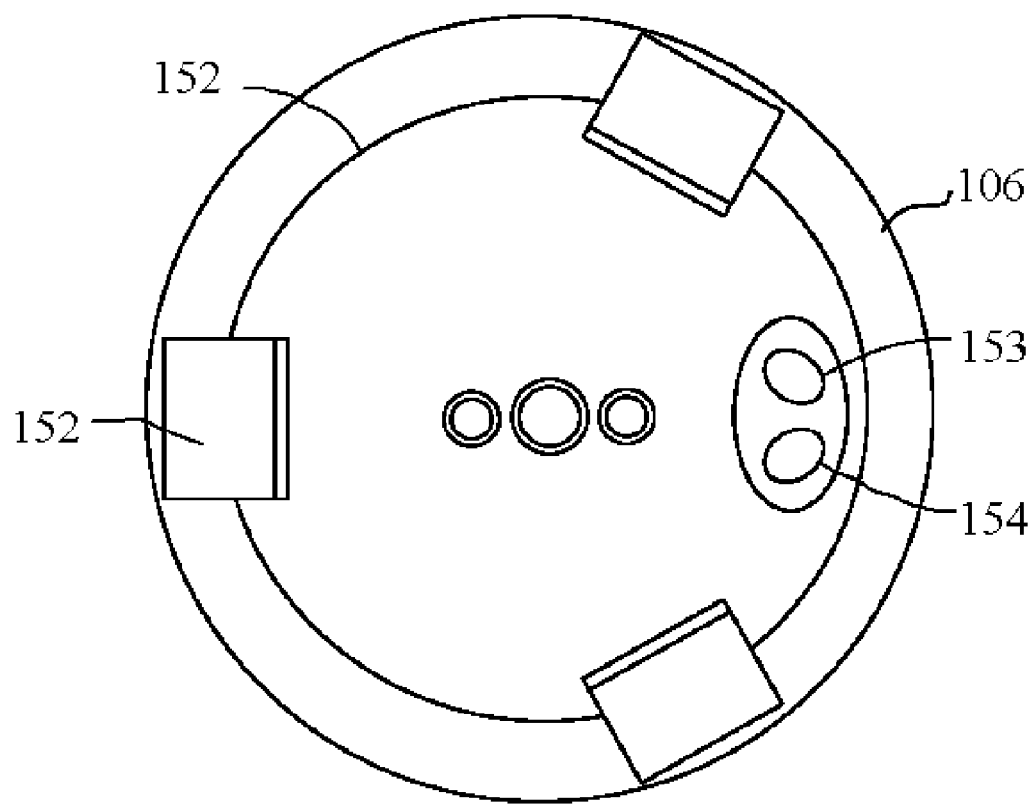

In the first embodiment, the probe 106 is a hardware that can be firmly mounted on a shaking platform of an incubator/shaker with screws. To hold a medium container 500 firmly on the top of probe 106, a medium container clamp or fixture is required for probe 106. For example, a culture flask clamp 152 as shown in FIGS. 2a and 2b is mounted on the top of the probe 106 using screws 156. The clamp 152 can be an existing clamp in market with a minor modification to allow the aperture 153 and 154 open to a medium container. The probe enclosure 107 could be firmly mounted on a shaker platform through its center hole with a screw 157. The probe 106 may even include a temperature sensor and an electrical heater to keep light source 110 or/and photodetector 120 at a constant temperature that is usually above ambient temperature. To control the temperature of light source 110, the light source could be mounted inside of a metal enclosure and a temperature sensor and an electric heater are mounted inside and outside of the metal enclosure, respectively. The metal enclosure should be insulated. The heater can be a resistor. The enclosure should have an open aperture to allow the light going out from source 110. The enclosure may also include a light tunnel or/and lens for light beam formation.

In the first embodiment, the probe 106 can fit different size culture flasks. Due to its flat top design, probe 106 can hold a same or smaller size culture flask in diameter by mounting a matched clamp on its top. The clamp 152 is required to be mounted on a proper location to allow the incident light beam to go through the bottom corner of flasks.

Figure 3:
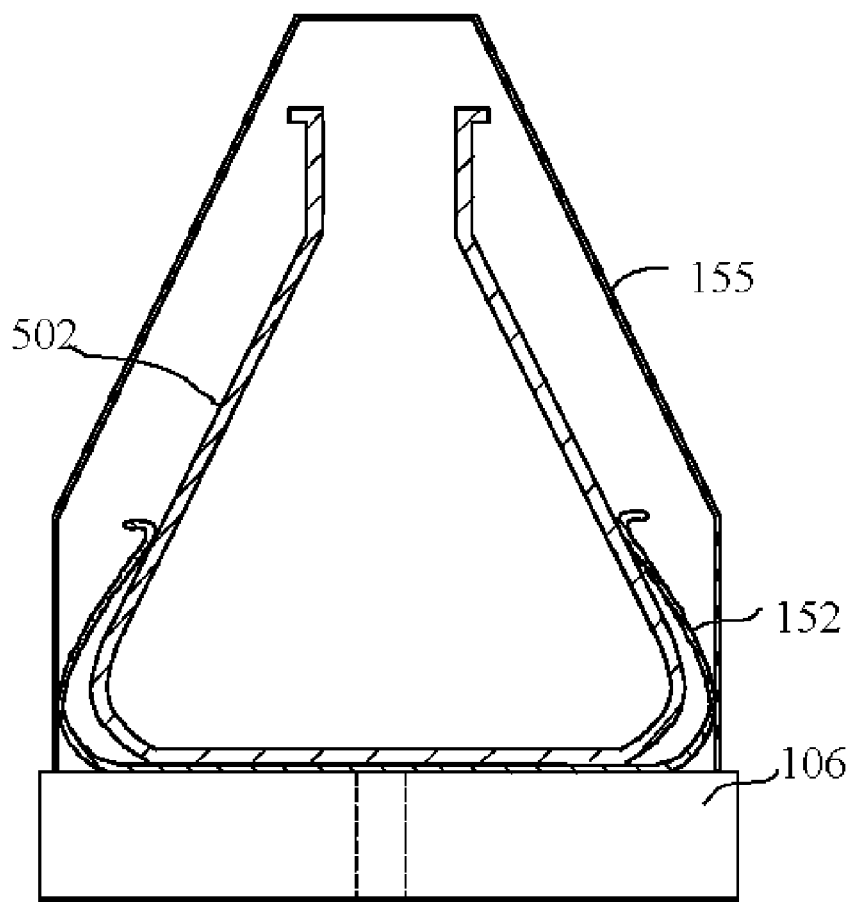
FIG. 3 A schematic diagrams of a light scattering probe with a flask clamp and a dark shield cover.
Figure 5:
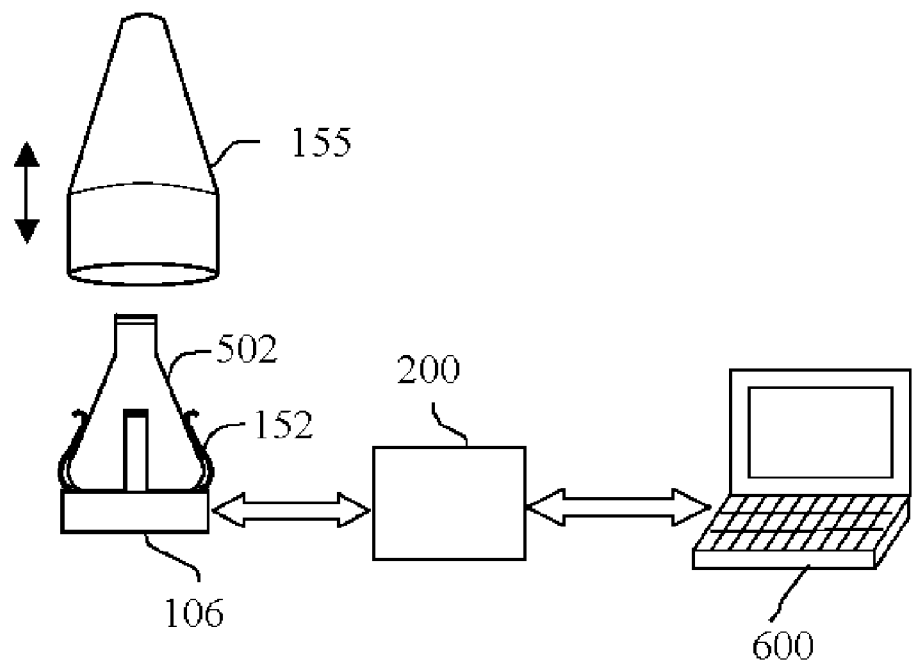
FIG. 5 A schematic diagram of a standalone cell culture monitoring system with one detecting probe for flask biological culture applications.

In the first embodiment, the probe 106 may have an opaque dark cover with it to shield the culture medium container from outside ambient light. This dark cover is a movable cover that can be moved away after measurement. This dark cover can largely reduce and even eliminate the ambient light influence to the measurement of the monitoring system. When the medium container 500 is a culture flask 502, the dark opaque cover 155 could be a circular cup shape as schematically shown in FIG. 3 and FIG. 5. Dark cover 155 can be made from thin opaque plastic or paper. The inside color of the dark cover 155 should be dark black. As an alternative, an opaque wall of container 500 with an opaque stopper except the transparent part at its bottom could reduce ambient light influence without the opaque dark cover 155. To compensate the ambient light, the ambient light could be detected using photodetector 120 when light source 110 is turned off shortly. The differential measurement between the turn-on and turn-off states of light source 110 could reduce the influence of the ambient light.

In the first embodiment, probe 106 may include a shaking sensor switch that can send an ON or OFF signal to the culture monitoring system when probe 106 is under a shaking or non-shaking condition. The shaking sensor could be a vibration/motion sensor or an acceleration sensor.

In general, a probe of the culture monitoring system includes a light source, a photo detector, a mechanical structure for housing, positioning and orientating the light source and the photodetector, a circuit for the light source and photodetector, a mechanical fixture for binding a removable culture container with the mechanical structure together during the monitoring process, and an opaque enclosure for shielding the container from ambient light.

In the second embodiment, a probe as described in the first embodiment may have two pair of light source 110 and photodetector 120 located in different places within a probe. For example, the probe may have two light sources with two different emission wavelengths such as 650 nm and 780 nm, respectively. The IR light source with 780 nm or other wavelength makes the probe more sensitive to cells with big size such as mammalian and yeast cells. A UV light source with 280 nm or other wavelength makes the probe sensitive to proteins.

Figure 4:
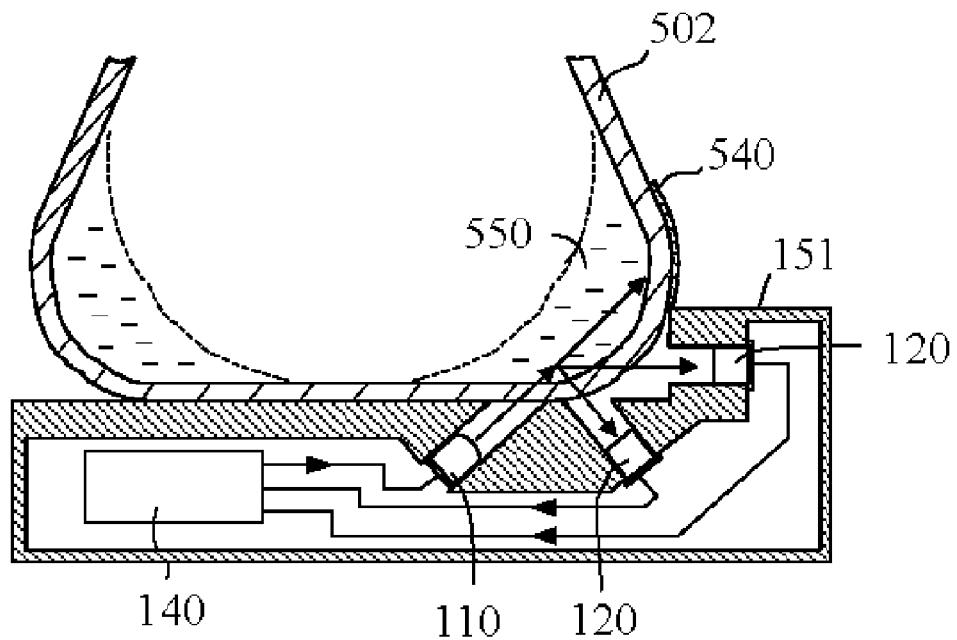
FIG. 4 A schematic diagram of a multi-angle scattering detection probe.

In the third embodiment, a probe 151 can be constructed for multi-angle scattering detection as schematically shown in FIG. 4. The probe 151 comprises a light source 110, two photodetectors 120 and electronic circuitry 140. One photodetector is designed for a small angle (<60°) scattering detection and the other for a large angle ($\geq$60°) scattering detection. A multi-angle scattering detection may allow its monitoring system to detect more cell properties such as the contents and morphology of cells. In FIG. 4, the dash line in flask 502 shows a typical air-medium interface curve when the medium with the container are in an orbital shaking circumstance. Furthermore, to reduce the reflection noise caused by the outside surface of the flask 502, a light absorption layer 540 (a black color paint) can be utilized on the small area that the incident light beam of source 110 strikes.

In the fourth embodiment, a typical standalone cell culture monitoring system mainly comprises one or more probes 106, a signal processing module 200 and a computer 600 as shown in FIG. 5. For flask culture in a typical incubator/shaker, the system also includes a culture flask 502, a flask clamp 152 and an opaque dark cover 155 that has a cup shape. Module 200 may comprises power supplies for probe 106, a signal conditioner, a user interface panel or buttons and its circuitry, a digital LED display, an alarm buzzer and a data acquisition circuitry that including an A/D converter and digital communication I/O. The communication I/O can be USB or RS232 or Ethernet that can be connected to computer 600 via wire or wireless method.

Figure 6:
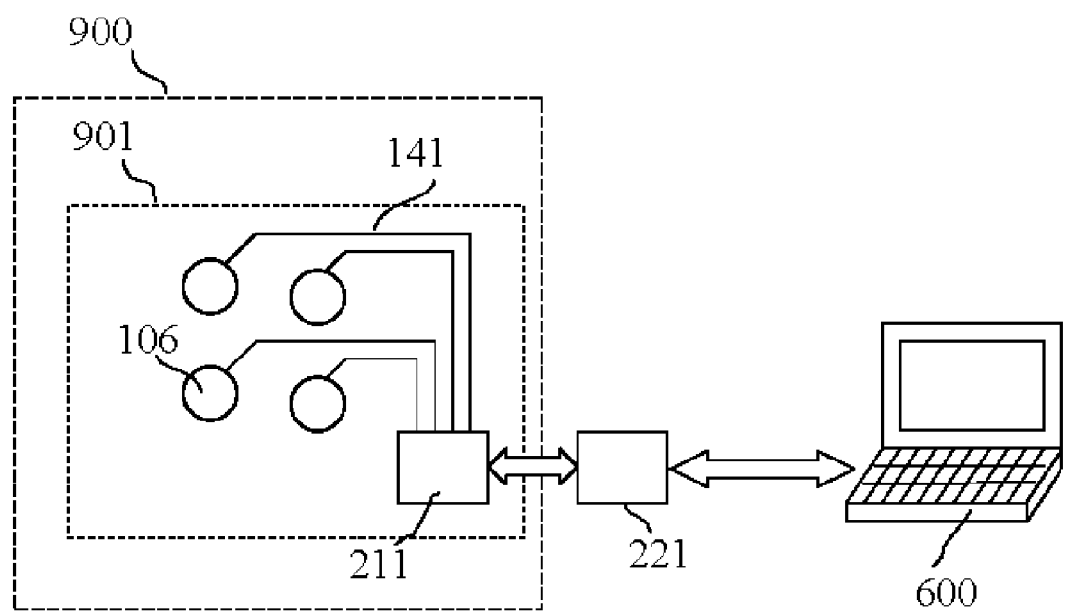
FIG. 6 A schematic diagram of a standalone scattering light monitoring system with multiple detecting probes for flask biological culture applications.

In the fifth embodiment, one or multiple probes 106 could be mounted on an incubator/shaker platform 901. As schematically shown in FIG. 6, a signal-processing module 211 is also mounted on incubator/shaker platform 901 and a module 221 is mounted outside of the incubator/shaker 900. In one option, module 211 comprises basically power supplies for several probes 106, a multiple channel A/D converter and a digital communication I/O. Module 211 may also include a reference photodetector for ambient light compensation, a temperature sensor or/and a shaking sensor. Module 221 may comprise a power supply for module 211, a user interface panel or buttons, an alert buzzer or a digital LED display. Module 221 can also include a wireless transceiver to communicate with computer 600 that is also equipped with a wireless transceiver. In another option, a one-channel A/D converter, a digital I/O and a digital communication I/O circuitry are included in module 221 instead of in module 211. Module 211 includes a multichannel switch circuitry that allows only one probe 106 to send its signal to the A/D converter at each time. So the multiple probe signals will be converted to digital signal at the A/D converter at different and consecutive time frame.

For example, if the sampling time interval is one second and there are three probes, the switch will let the A/D converter to take the first probe data at the first second, the second probe data at the second second, the third probe data at the third second, and then repeat the above switching processing. The switch circuitry can be controlled by computer software through the digital I/O in module 221.

Figure 7:
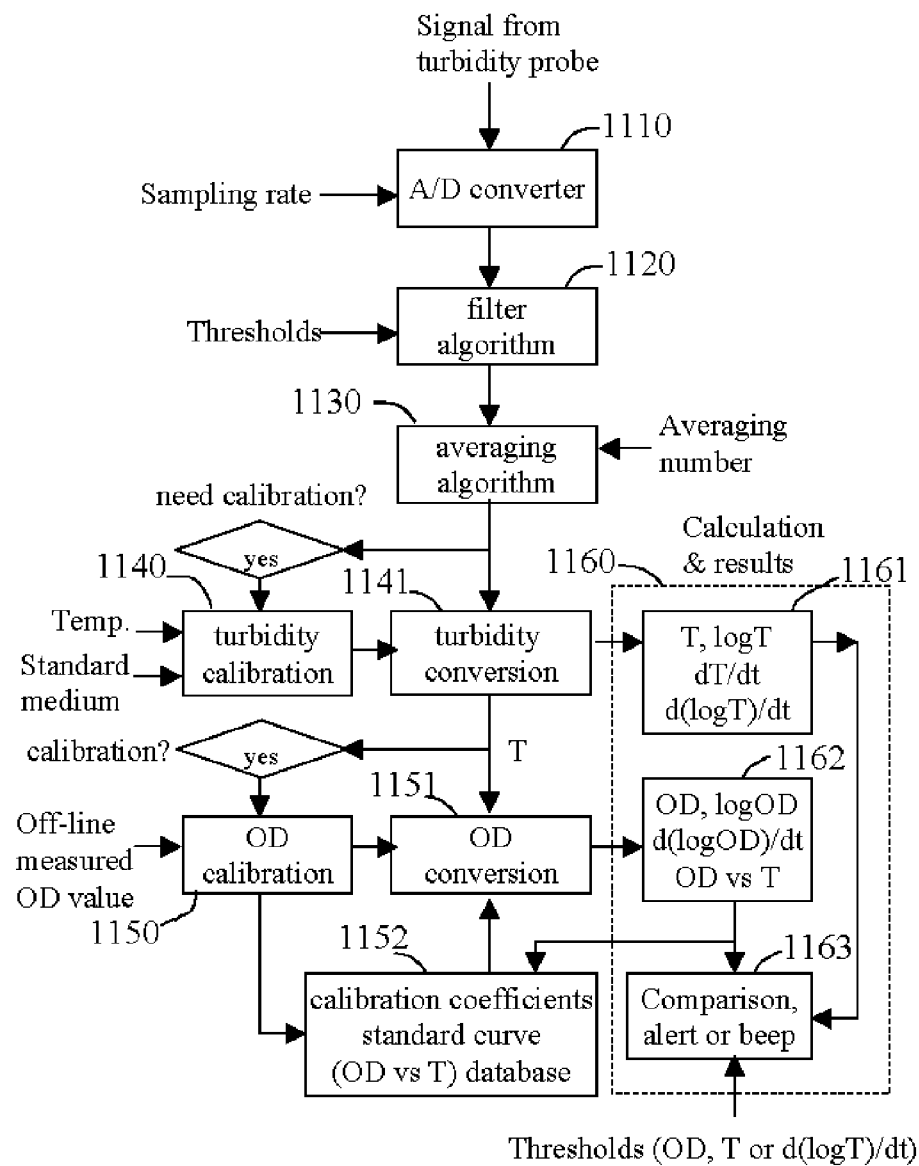
FIG. 7 A flow chart of a typical signal and data processing system for a turbidity monitoring system.

In the sixth embodiment, mainly for cell culture turbidity measurement, a typical detector signal and data processing system after the signal amplification is shown schematically in FIG. 7. It mainly comprises A/D conversion 1110, filter process 1120, moving average process 1130, scattering turbidity calibration 1140 if needed, scattering turbidity conversion 1141, Optical Density (OD) calibration 1150 if needed, OD conversion 1151, standard curve (a curve of OD versus scattering turbidity) and calibration coefficient database 1152, result presentation 1160 including growth rate calculation and alert action besides the turbidity and converted OD. An A/D converter can perform A/D conversion 1110 at a specific sampling rate that can be controlled by a microprocessor or a computer. For example, the sampling rate can be set to take one data point in one second by the A/D converter. In this signal and data processing system, process 1140, 1141, 1150 and 1151 are not necessary if only for monitoring a growth curve in an arbitrary unit.

In the sixth embodiment, the filter algorithm 1120 could be a clip programs that eliminating a sharp peak noise when a signal data is larger than a specific deviation or value. However the clip method may not be enough. Usually the sharp high intensity noise caused by the bubbles, air-medium interface reflection or the scattering non-uniformity of a turbulent biological medium can cause a huge signal fluctuation. It is found that the most noises cause electronic signal to fluctuate in only high value direction instead of randomly in both high and low directions. Therefore a simple filter algorithm is utilized in the monitoring system. The method is to choose only a few of lower value data points in every specific number of sampling data points and abandon the rest data points. This method can be realized by perform a sorting algorithm in every specific number of sampling data. For example, for every ten sampling data points, the program of the monitoring system will make a sort by data values and then choose only two smaller value data points (such as the second and third smallest value data) for further process.

In the sixth embodiment, the data after passing the filter algorithm can be processed using an averaging algorithm to enhance signal to noise (S/N) ratio. An average processing such as a consecutive moving average can greatly suppress the shaking medium noise. Above filtering and averaging techniques are benefited by taking high sampling rate data with respect to a slow biological culture growth rate because the turbidity or other measurable properties of the biological culture medium may approximately be a constant in a very short period such as in tens of seconds. In such short period, as many as hundreds of discrete data points can be acquired. After the filtering and averaging processes, the output data values are still in original data unit such as voltage. These original data are still individual probe and culture container dependent. So the monitoring system may require a standard turbidity calibration to generate standardized scattering turbidity values for each probe.

In the sixth embodiment, the calibration for the scattering turbidity measurement system may have two different steps. The first step is a turbidity calibration 1140. This step is optional. However this turbidity calibration is necessary for keeping the turbidity measurement comparable for different turbidity monitoring systems or the same system but in different time or conditions. Turbidity calibration is a process to let the probe 106 and its post signal processing device give comparable and standardized turbidity values for medium turbidity. After this calibration, the monitoring system can convert its original scattering intensity (turbidity) values such as voltage to standardized turbidity values. The calibration is carried out by measuring the original scattering intensity value of a standard medium in a medium container 500 with its known standard turbidity value. The standard medium can be the same formula solution with different values of turbidity through dilution so that multiple-point calibration can be performed. Usually, two-point calibration is enough for the scattering turbidity in a linear range. For example, one point is the zero-turbidity point and the other is a standard turbidity point such as 400 NTU. The standard medium can be a primary standard solution, Formazin or other turbidity standard. After the turbidity calibration, the monitoring system can calculate and generate the standardized turbidity values from the original measurement values based on the calibration numbers. For example, after a two-point linear calibration, one point is the zero-turbidity point and the other is a standard turbidity point 400 NTU, the monitoring system can convert an original value X to a standardized turbidity value T using following equation: $T=400(X-X_0)/(X_{400}-X_0)$, where $X_0$ and $X_{400}$ are measured original values at zero and 400 NTU turbidity, respectively.

The second step is a calibration between biological cell concentrations and the standardized turbidity values or original scattering intensity values. If an off-line transmission OD measurement is utilized to represent the biological substance concentration, the second step is a calibration between the off-line OD and the scattering turbidity values for specific biological medium because the calibration results could be different for different biological medium or even different spectrophotometers. In a linear measurement range, two-point calibration should be enough. For measurements out its linear range, more than two point calibration is required. Generally, the relation (standard curve) between the off-line OD measured by a spectrophotometer and the turbidity value measured by the turbidity monitoring system can be expressed using a polynomial expression after a curve fit. This OD calibration should be spread out from low to high biological medium concentration. This OD calibration can be carried out with help of a microprocessor or a computer. The process may comprises steps of:

making at least two set measurements on the turbidity value from the monitoring system and the corresponding optical density from a spectrophotometer for the biological culture medium with different concentration;

using the microprocessor or computer to calculate the coefficients of a pre-defined equation based on the above measurements. The calculation may include a curve fit technique. The number of the measurement set should be equal to or larger than the number of the coefficients that are needed to solve. Generally, the pre-defined equation is a polynomial equation.

In the sixth embodiment, OD conversion 1151 is a calculation process based on obtained OD calibration coefficients and the pre-defined equation such as a polynomial equation. The OD calibration coefficients can be uploaded from previous cell culture calibration that have saved the coefficients in database 1152 or an OD calibration file. The OD calibration coefficients can also be updated after a real-time OD calibration process 1150. The monitoring system software can allow users to update or upload OD calibration coefficients in anytime during a real-time cell culture monitoring process.

Figure 8:
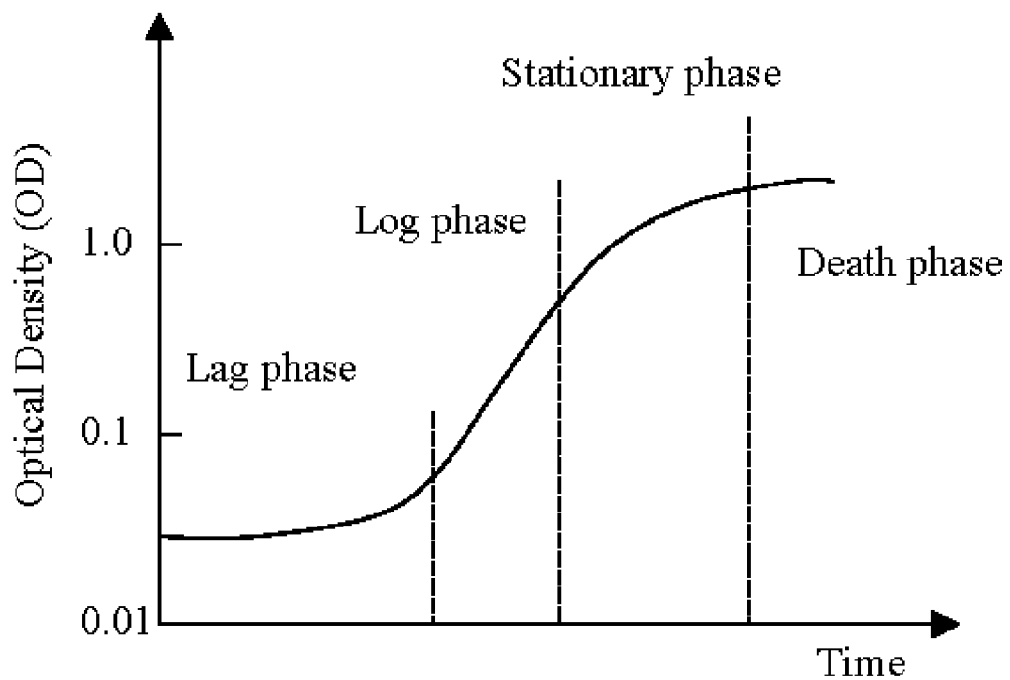
FIG. 8 A typical growth curve in term of the OD of biological culture versus the incubation time.
Figure 9:
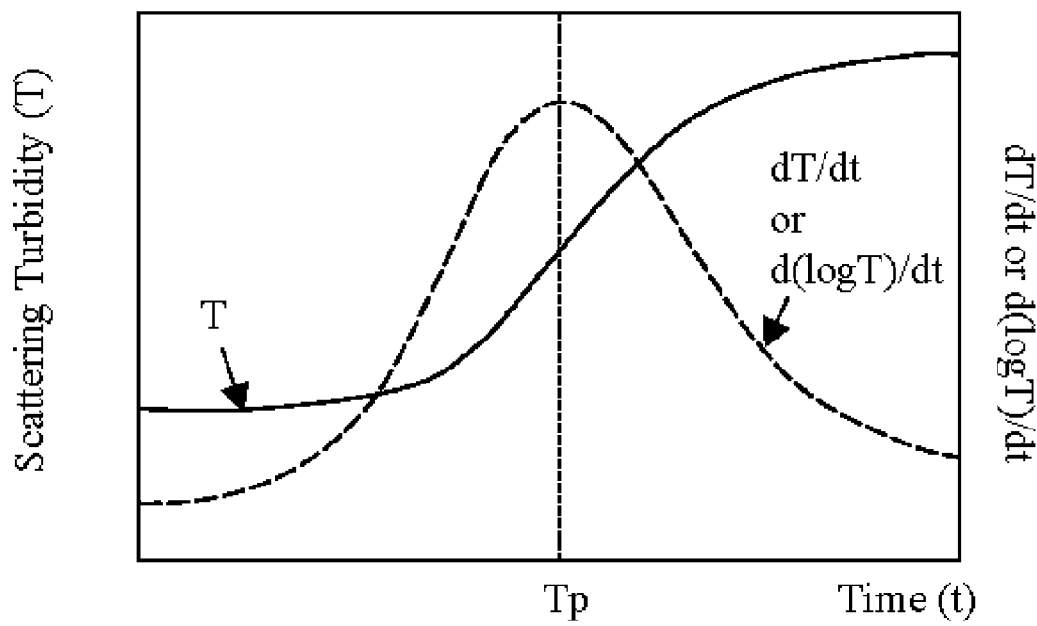
FIG. 9 Typical growth curve and growth rate in term of the scattering turbidity of biological culture.

For batch microbial culture such as shaking flask culture, a typical growth curve of microorganisms is shown in FIG. 8. This growth curve could be the optical density (OD) versus the incubation time. The microorganisms experience four phases: lag phase, log phase, stationary phase and death phase. In the lag phase, microorganisms grow slowly and are acclimated to their new habitat. In the log phase, the number of microorganisms increases exponentially. In the stationary phase, the viable number of microorganisms becomes stabilized. In the death phase, the viable number of microorganisms decreases. Because the transmission OD reflects the total biomass density including dead microorganisms, the OD values still increase in the stationary and death phase. The scattering turbidity measurement can also generate similar growth curves of microorganisms and cells as shown in FIG. 9. The growth curve can easily show information about when the microorganisms are in the first three phases. This information is very important for some biological processes such as recombinant protein expression in microorganisms. To optimize the protein production, induction of protein expression at a right time or a right growing phase for microorganism is required. It is expected to maximize viable biomass and minimize metabolic byproducts. Usually, inducers are added when microorganism culture $OD_{600}$ reaches a value between 0.4 and 1. The optimal OD value depends on the culture method and the medium.

In the sixth embodiment, apart from monitoring concentration in term of measured scattering turbidity or converted OD, this turbidity monitoring system can send out an alert signal such as beeps when the OD or the scattering turbidity T reaches a preset threshold value. Apart from the OD or scattering turbidity T, their log expression log(OD) and log(T), as well as growth rate d(OD)/dt, dT/dt (or d(log(OD))/dt, d(logT)/dt) are also be very useful. The growth rate dT/dt is the slope, or say, derivative of the scattering turbidity with respect to the incubation time. The expression d(logT)/dt is the derivative of the turbidity logarithm with respect to the incubation time. Note that the growth rate defined here is different from Specific Growth Rate. The growth rate value usually peaks when microorganisms or cells are in a transition from the log phase to the stationary phase as shown in FIG. 9. So the peak-time Tp could be a very useful quantity or reference point for the induction of protein expression. An alert signal or beeps can be activated when the growth rate peaks. This can be realized by software embodiment that performing a moving linear fit for specific number of measured turbidity points and then obtaining a slope value of the linear fit. The continuation of the moving linear fit can generate a real-time growth rate curve with respect to incubation time. In this embodiment, derivative d(OD)/dt or d(log(OD))/dt can also be obtained in real-time.

Light scattering at wider angles such as a right angle to incident light beam may be able to provide information about internal contents of cells. For one specific application, the monitoring system could provide a novel method to detecting the protein inclusion bodies in real-time during culture process. It is known that a high level of cytoplasmic granularity of cells will give higher scattering intensity at a wide angle. Then the ratio of the scattering intensity to transmission or small angle scattering intensity should be increased. For example, cells that are cultivated to produce foreign proteins may deposit the proteins as inclusion bodies. These highly refractive inclusions increase wide-angle scattering intensity. Therefore the ratio of the right angle to forward scattering signal or transmission signal from cells with inclusion bodies could be differentiated from cells without the inclusion bodies.

In the seventh embodiment, the probe of the monitoring system has at least two photodetectors as described in the third embodiment. The difference between two photodetector signals may be utilized for protein inclusion body detection. Even with only one large-angle-scattering photodetector as described in the first embodiment, the monitoring system could also detect the inclusion bodies because the transmission signal OD can be measured with an off-line spectrophotometer. In the sixth embodiment of this invention, a standard curve, or say, OD calibration curve that is a calibrated relation between OD value and scattering turbidity, such as the curve of the OD value versus the scattering turbidity. This standard curve is also valuable information besides the scattering turbidity and OD. Because the standard curve varies for different cell species. With the help of a microprocessor or computer, the standard curve for different cell species in various culture conditions could be saved in a file or database. These data can also be used for the OD conversion if the same biological culture process with the same medium and substance is repeated. For inclusion body detection, an off-line OD measurement is required for a probe with a single photodetector. The change from the standard curve of the same kind of cells without inclusion bodies may indicate the inclusion bodies in the cells.

In the eighth embodiment, a temperature compensation method for probe 106 is employed when probe 106 does not have a temperature control in its enclosure 107 or temperature is out of some limits. As we know, different biological culture may require different culture temperature. A typical incubated shaker may have a working range from ambient temperature to 60° C. Some incubated shaker can work from temperature below zero degree to 70° C. The sensitivity of probe 106 will change significantly if it is undergoing a large temperature change that may be caused by the intensity drift of light source 110 or the sensitivity change of photodetector 120. So a temperature compensation method is necessary for this kind of applications. This temperature compensation can be achieved by adjusting the turbidity calibration factors such as $X_0$ and $X_{400}$ described in the sixth embodiment for different temperature. The turbidity monitoring system may store a temperature coefficient curves that is the original data values of a calibration standard as a function of the temperature such as $X_{400}$ versus temperature. This temperature coefficient curve is obtained by doing turbidity calibration for a known turbidity standard with different temperatures and performing a curve-fit calculation. Then a turbidity value from the monitoring system will be calculated based on the temperature and the corresponding calibration factors.

In the ninth embodiment, apart from the total cell concentration, the viable cell concentration in the biological culture medium could be monitored. For some cell species, its light scattering intensity in a turbulent shaking state or a fast shaking state is significantly different from a non-turbulent state including a slow shaking or a quasi-stationary state just after a fast shaking state. Furthermore the difference may be related the viable cell concentration. Thus in this embodiment, the shaking speed is purposely turned to a high, low or off value during the biological cell culture. The culture monitoring system can also be programmed to separate the scattering data of a high speed shaking state from a short period of non-shaking state automatically based on the shaking speed value from the shaking speed sensor.

Figure 10:
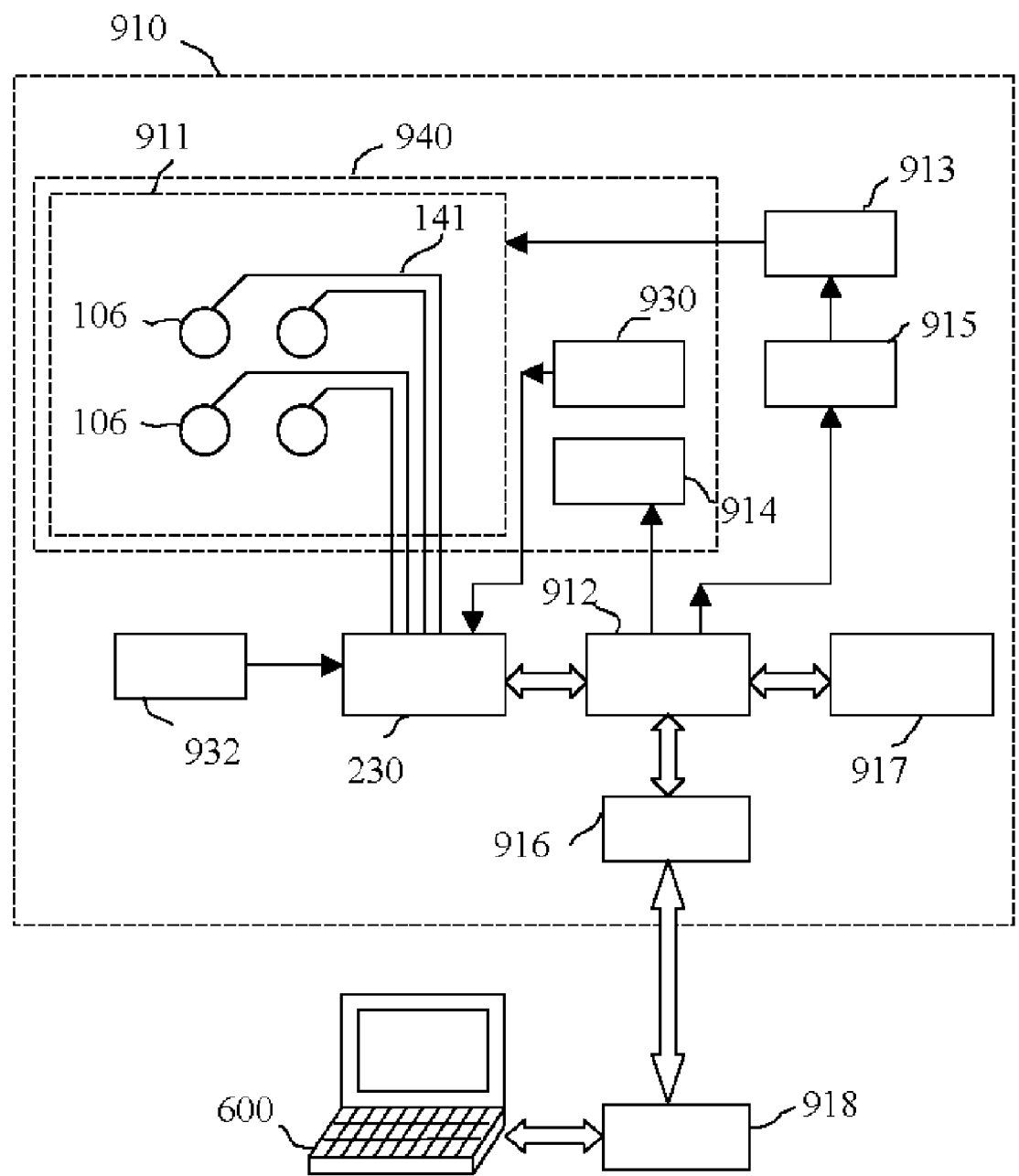
FIG. 10 A block diagram of an advanced incubated shaker with integrated culture turbidity monitoring detectors.

In the tenth embodiment, the combination of the cell culture monitoring system and a conventional culture incubated shaker could provide an innovative equipment for biological culture. FIG. 10 schematically shows a block diagram of such advanced incubated shaker 910. Either one probe 106 or multiple probes 106 are mounted on or embedded in the shaker platform 911. A module 230 that includes an A/D converter and power supply for the multiple probes can perform signal processing for probes 106, a temperature sensor 930 and a shaking speed sensor 932 together. The shaking speed sensor may not be necessary because the speed information can be obtained from the shaker motor driver or its control circuitry. Electronic control module 912 that including a microprocessor can not only perform data processing for signals from probes 106, the temperature sensor 930 and the shaking speed sensor 932, but also send control signals to a shaker motor driver 915 and a temperature control module 914 to regulate shaking motor 913 speed and the temperature of incubator/shaker culture space 940. The temperature control module 914 can include electrical heater, cooler or both. The incubated shaker 910 can also includes a digital communication I/O 916 for connection with a computer 600. The digital communication I/O 916 may include a RF wireless transceiver to communicate with computer 600 via another RF wireless transceiver 918 that connected to computer 600. The communication can also be carried out with a wire without using RF wireless transceivers. The simple way is to utilize RS-232, RS-485, Ethernet or USB wire connection. This embodiment can also allow probe cables 141 to be easily connected within incubated shaker 910. The shaker 910 may also includes display and user-interface module 917. As a conventional incubated shaker, the shaking speed, temperature and timer can be preset and displayed through module 917. Furthermore, the module 917 can be designed to show the growth curve and growth rate of biological culture, or just turbidity value or converted OD value. Module 917 may include a buzzer. An alert threshold for the turbidity or converted OD can also be preset with module 917. When the turbidity of biological culture reaches the threshold, an alert signal such as beeps will be sent out through module 917. With the integration of the turbidity monitoring system and the conventional incubator/shaker, the incubator shaker 910 can be programmed to automatically change its temperature, shaking speed or both based on its measured real-time turbidity or converted OD values in order to change the growth rate of biological culture.

In the eleventh embodiment, an opaque enclosure or cover is utilized to replace typically transparent cover of the incubated shaker. This can eliminate ambient light influence. The culture space in the incubated shaker 910 is optically isolated from outside of the shaker when the cover is closed.

In the twelfth embodiment, the cover of the incubated shaker is also constructed as an optical filter that can significantly block some specific wavelength of ambient light. The wavelength of the light source 110 of the turbidity monitoring system is just in the blocked wavelength region. When the photodetector 120 has a narrow band pass filter on the light source 110 wavelength, the ambient light will have less effect on the photodetector 120. For example, if a blue transparent cover only allows blue color light to go through, the light source 110 has a different color such as a red color light beam and the photodetector 120 also has a red color pass filter, the influence of ambient light can then be significantly reduced.

While the invention has been described in conjunction with the preferred embodiments, features and methods, it should be noted that many alternatives, novel features, novel combination, modifications and variations are apparent to those skilled in the art. Accordingly, the preferred embodiments and description in the invention set forth above are intended to be illustrative and not limiting. Various changes may be made without departing from the spirit and scope of the application.

What is claimed is:

1. An apparatus for on-line monitoring biological culture medium in an orbital shaking environment of an incubator/shaker, comprising:
   a container that can hold a liquid biological culture medium in which biological cells are incubated, and at least a part of the container's wall is optically transparent;
   at least one light emission source means for emitting light to interact with said biological culture medium through the transparent wall of said container;
   at least one photodetector means for directly detecting scattered or transmitted light by said biological culture medium through the transparent wall of said container when the emitted light from said light emission source interacts with said biological culture medium;
   a probe fixture means for mounting and orientating at least one said light emission source and at least one said photodetector in fixed positions relative to each other, and for holding said container firmly without any relative movement with respect to said light emission source, said photodetector and a shaking platform of said incubator/shaker during the on-line monitoring process while said container and the probe fixture are under a continuously shaking condition;
   detecting means for detecting one and/or more properties of said biological culture medium, one of said properties is the cell concentration in said biological culture medium;
   processing means for amplifying electrical signal from said photodetector, and then for further processing the signal and presenting the properties of the biological cell culture.

2. An apparatus of claim 1, wherein said properties of the biological culture medium for detection include the fluorescence of the cells in the biological culture medium, wherein said photodetector further including an optical filter.

3. An apparatus of claim 1, wherein said properties of the biological culture medium for detection include the protein inclusion bodies in biological cells.

4. An apparatus of claim 1, wherein said light emission source is a diode laser with a focus lens for generating a laser beam, wherein said photodetector is a photodiode.

5. An apparatus of claim 1, wherein said processing means including means for analog signal to digital data conversion and a microprocessor means for digital data processing, and wherein the digital data processing further including a filter algorithm for filtering large fluctuation noise caused by shaking culture medium and a moving averaging algorithm for reducing signal fluctuation.

6. An apparatus of claim 1, wherein said probe fixture means further including:
   a container clamp means for holding the container;
   a detection probe means for housing said light emission source and said photodetector and positioning the photodetector relative to the light emission source, and further for housing circuit means for detecting and amplifying electrical signal from the photodetector;

a mounting means for firmly attaching the clamp means with the detection probe means so that the light source and photodetector are positioned around the bottom corner of the container;

a light guide means for narrowing the irradiation and viewing angle of the light emission source and the photodetector, respectively;

a dark shield cover means for reducing ambient light into the container.

7. An apparatus of claim 1, wherein said container is an Erlenmeyer flask.

8. An apparatus of claim 1, further including more than one probe fixtures and one or more signal processing module means for processing and transferring signals between the multiple probe fixtures and a computer via wires or wireless means.

9. An apparatus of claim 1, wherein the probe fixture is further integrated with the shaking platform of the incubator/shaker, and wherein said processing means is integrated with the circuit of the incubator/shaker.

10. An apparatus of claim 1, wherein said processing means further including means for controlling and regulating the shaking speed and temperature of the incubator/shaker based on the monitoring results of the biological cell culture.

11. A method for on-line monitoring biological culture medium in an orbital shaking environment of an incubator/shaker, comprising:

utilizing a container to hold a liquid biological culture medium in which biological cells are incubated, and at least a part of the container's wall is optically transparent;

positioning a light emission source relative to the transparent wall of said container and irradiating light through the wall of said container and interacting with said biological culture medium;

positioning and aiming at least one photodetector to detect light from the interacting section of the incident light with the biological culture medium;

fixing the position of said photodetector with respect to said light emission source outside of said container;

preventing the relative movement of said container with respect to the position of the light emission source, the photodetector and the shaking platform of the incubator/shaker during the on-line monitoring process while said container and the probe fixture are under a continuously shaking condition;

providing monitoring means for monitoring one and/or more properties of said biological culture medium, one of the properties is the cell concentration in said biological culture medium;

providing processing means for amplifying electrical signal from said photodetector, and for further processing the signal and presenting the properties of the biological cell culture.

12. A method of claim 11, wherein said properties of the biological culture medium for monitoring include biological cell growth curve and growth rate, wherein further comprising a step of calculating the turning point of the biological cell growth from a log phase to a saturation phase.

13. A method of claim 11, wherein said properties of the biological culture medium for monitoring include the protein inclusion bodies in biological cells, wherein further comprising a step of making differential detection between a small angle scattering and a larger angle scattering.

14. A method of claim 11, wherein said properties of the biological culture medium for monitoring include the viable cell concentration in the biological culture medium, comprising a further step of making differential measurement with biological culture medium between a turbulent shaking and a non-turbulent circumstances.

15. A method of claim 11, wherein further comprising steps of:

arranging the location and emission angle of the incident light from said source to submerge in the culture medium, and avoid its light path to go through the interface between the culture medium and air directly in the container when the biological culture medium is under continuously shaking condition;

aiming the photodetector to the entry or near entry area of said interacting section;

narrowing the irradiation and viewing angle of the light emission source and the photodetector, respectively;

providing an opaque shield cover means for reducing ambient light into the container.

16. A method of claim 11, wherein further comprising a step of utilizing digital data processing algorithms to enhance signal to noise ratio and reduce the fluctuation noise when the biological culture medium is shaken, wherein further including the steps of:

filtering high value noise with a data sorting algorithm;

reducing signal fluctuation with a moving averaging algorithm.

17. A method of claim 11, wherein further comprising a step of performing data conversion from original signal data to standardized scattering turbidity values for biological culture medium through calibration process with a known turbidity standard.

18. A method of claim 11, wherein further comprising a step of performing data conversion from signal data to optical density for biological culture medium through calibration process that comprising the steps of:

making at least two set measurements on signal data and the optical density from an off-line spectrophotometer for the biological cells with different concentration;

calculating the coefficients of a polynomial expression for the calibration through a curve fitting process based on the above measurements, wherein the number of the measurement set should be equal to or larger than the number of the coefficients.

19. A method of claim 11, wherein further comprising the steps of:

embedding the light emission source and the photodetector in the shaking platform of an incubator/shaker;

integrating the signal and data processing means with the circuit of the incubator/shaker.

20. A method of claim 11, wherein further comprising control means for automatically controlling the shaking speed and the temperature of the incubator/shaker based on the monitoring results of the biological cell culture.

* * * * *